United States Patent
Gong et al.

(10) Patent No.: US 11,534,141 B2
(45) Date of Patent: Dec. 27, 2022

(54) METHODS FOR ENCODED MULTI-PULSE CONTRAST ENHANCED ULTRASOUND IMAGING

(71) Applicant: Mayo Foundation for Medical Education and Research, Rochester, MN (US)

(72) Inventors: Ping Gong, Rochester, MN (US); Shigao Chen, Rochester, MN (US); Pengfei Song, Champaign, IL (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 362 days.

(21) Appl. No.: 16/633,750

(22) PCT Filed: Jul. 26, 2018

(86) PCT No.: PCT/US2018/043829
§ 371 (c)(1),
(2) Date: Jan. 24, 2020

(87) PCT Pub. No.: WO2019/023422
PCT Pub. Date: Jan. 31, 2019

(65) Prior Publication Data
US 2021/0085293 A1    Mar. 25, 2021

Related U.S. Application Data

(60) Provisional application No. 62/537,107, filed on Jul. 26, 2017.

(51) Int. Cl.
*A61B 8/08* (2006.01)
*G01S 7/52* (2006.01)
*G01S 15/89* (2006.01)

(52) U.S. Cl.
CPC .......... *A61B 8/481* (2013.01); *G01S 7/52039* (2013.01); *G01S 15/8915* (2013.01);
(Continued)

(58) Field of Classification Search
CPC .......................... A61B 8/481; G01S 15/8963
See application file for complete search history.

(56) References Cited

U.S. PATENT DOCUMENTS 5,851,187 A * 12/1998 Thomas, III ........ G01S 15/8959
600/443
6,048,315 A *  4/2000 Chiao ................. G01S 15/8997
600/447
(Continued)

OTHER PUBLICATIONS

Tiran [Multiplane Wave Imaging Increases Signal-To-Noise Ratio in Ultrafast Ultrasound Imaging, Phys. Med. Biol. 60 (2015) 8549-8566] (Year: 2015).*
(Continued)

*Primary Examiner* — Oommen Jacob
(74) *Attorney, Agent, or Firm* — Quarles & Brady LLP (57) ABSTRACT

Methods for contrast-enhanced ultrasound imaging that implement coded multi-pulses in each of two or more different transmission events are described. Data acquired in response to the two different transmission events are decoded and combined. In some embodiments, the coded multi-pulses include two or more consecutive Hadamard encoded ultrasound pulses. In other embodiments, multiplane wave pulses can be used. Such multiplane wave pulses can be coded using Hadamard encoding, as one example. In addition, the multiplane wave pulses can be further coded using amplitude modulation, pulse inversion, or pulse inversion amplitude modulation techniques.

19 Claims, 8 Drawing Sheets

(52) U.S. Cl.
CPC ...... *G01S 15/8963* (2013.01); *G01S 15/8995* (2013.01); *G01S 15/8997* (2013.01)

(56) References Cited

U.S. PATENT DOCUMENTS

| | | | | |
|---|---|---|---|---|
| 8,641,628 | B2* | 2/2014 | Bradley | G01S 15/8927 600/443 |
| 9,504,449 | B2* | 11/2016 | Nicolas | G01S 15/8959 |
| 2003/0114758 | A1* | 6/2003 | Jensen | A61B 8/481 600/437 |
| 2013/0331699 | A1 | 12/2013 | Ishihara | |
| 2016/0061950 | A1* | 3/2016 | Xu | G01S 15/8997 342/25 A |
| 2021/0085293 | A1* | 3/2021 | Gong | G01S 15/8915 |

OTHER PUBLICATIONS

Eckersley ["Optimising Phase and Amplitude Modulation Schemes for Imaging Microbubble Contrast Agents at Low Acoustic Power", Ultrasound in Med. & Biol., vol. 31, No. 2, pp. 213-219, 2005]. (Year: 2005).*

Burns, P.N. et al, "Pulse inversion imaging of liver blood flow—Improved method for characterizing focal masses with microbubble contrast," Investigative Radiology, vol. 35, No. 1, pp. 58-71, Jan. 2000.

Couture, O. et al, "Ultrafast Imaging of Ultrasound Contrast Agents," Ultrasound in Medicine and Biology, vol. 35, No. 11, pp. 1908-1916, Nov. 2009.

Couture, O. et al, "Ultrasound Contrast Plane Wave Imaging," Ieee Transactions on Ultrasonics Ferroelectrics and Frequency Control, vol. 59, No. 12, pp. 2676-2683, Dec. 2012.

Eckersley, R.J. et al, "Microbubble contrast agent detection using binary coded pulses," Ultrasound in Medicine and Biology, vol. 33, No. 11, pp. 1787-1795, Nov. 2007.

Eckersley, R.J. et al, "Optimising phase and amplitude modulation schemes for imaging microbubble contrast agents at low acoustic power," Ultrasound in Medicine and Biology, vol. 31, No. 2, pp. 213-219, Feb. 2005.

Farrer A. I. et al., "Characterization and evaluation of tissue-mimicking gelatin phantoms for use with MRgFUS," Journal of Therapeutic Ultrasound, vol. 3, p. 9. 2016.

Gong, P., et al, "Advanced ultrafast imaging with synthetic transmit aperture (USTA) imaging," in 2016 IEEE International Ultrasonics Symposium (IUS), 2016, pp. 1-2.

Gong, P., et al, "Hadamard Encoded Multi-Pulses for Contrast Enhanced Ultrasound Imaging," ed: IEEE Transactions on Ultrasonics, Ferroelectrics, and Frequency Control, Aug. 2017.

Gong, P., et al. "Delay-encoded harmonic imaging (DE-HI) in multiplane-wave compounding." IEEE transactions on medical imaging 36.4 (2016): 952-959.

Gong, P., et al. "Improved contrast-enhanced ultrasound imaging with multiplane-wave imaging." IEEE transactions on ultrasonics, ferroelectrics, and frequency control 65.2 (Dec. 2017): 178-187.

Haider B. et al, "Higher order nonlinear ultrasonic imaging," in 1999 IEEE Ultrasonics Symposium. Proceedings. International Symposium (Cat. No. 99CH37027), 1999, vol. 2, pp. 1527-1531 vol. 2.

Horie, S. et al, "Contrast-enhanced high-frequency ultrasound imaging of early stage liver metastasis in a preclinical mouse model," Cancer Letters, vol. 339, No. 2, pp. 208-213, Oct. 2013.

International Searching Authority, International Search Report and Written Opinion for application PCT/US2018/043829, dated Oct. 23, 2018.

Leavens, C. et al, "Golay Pulse Encoding for Microbubble Contrast Imaging in Ultrasound," IEEE Transactions on Ultrasonics, Ferroelectrics, and Frequency Control, vol. 54, No. 10, pp. 2082-2090, 2007.

Li, P.C. et al, "Waveform design for ultrasonic pulse-inversion fundamental Imaging," Ultrasonic Imaging, vol. 28, No. 3, pp. 129-143, Jul. 2006.

Lindner, J. R., "Assessment of resting perfusion with myocardial contrast echocardiography: theoretical and practical considerations," (in eng), Am Heart J, vol. 139, No. 2 Pt 1, pp. 231-240, Feb. 2000.

Montaldo, G. et al, "Coherent Plane-Wave Compounding for Very High Frame Rate Ultrasonography and Transient Elastography," Ieee Transactions on Ultrasonics Ferroelectrics and Frequency Control, vol. 56, No. 3, pp. 489-506, Mar. 2009.

Morgan, K. et al, "The effect of the phase of transmission on contrast agent echoes," Ieee Transactions on Ultrasonics Ferroelectrics and Frequency Control, vol. 45, No. 4, pp. 872-875, Jul. 1998.

Needles A. et al., "Nonlinear Contrast Imaging With an Array-Based Micro-Ultrasound System," Ultrasound in Medicine and Biology, vol. 36, No. 12, pp. 2097-2106, Dec. 2010.

Papadacci, C. et al, "High-Contrast Ultrafast Imaging of the Heart," Ieee Transactions on Ultrasonics Ferroelectrics and Frequency Control, vol. 61, No. 2, pp. 288-301, Feb. 2014.

Pasovic M. et al., "Broadband reduction of the second harmonic distortion during nonlinear ultrasound wave propagation," (in eng), Ultrasound Med Biol, vol. 36, No. 10, pp. 1568-1580, Oct. 2010.

Pasovic M. et al., "Second harmonic inversion for ultrasound contrast harmonic imaging," Physics in Medicine and Biology, vol. 56, No. 11, pp. 3163-3180, Jun. 2011.

Phillips P.J. et al, "Contrast pulse sequences (CPS): imaging nonlinear microbubbles," in 2001 IEEE Ultrasonics Symposium. Proceedings. An International Symposium (Cat No. 01CH37263), 2001, vol. 2, pp. 1739-1745 vol 2.

Shen C.C. et al, "Golay-Encoded Excitation for Dual-Frequency Harmonic Detection of Ultrasonic Contrast Agents," Ieee Transactions on Ultrasonics Ferroelectrics and Frequency Control, vol. 58, No. 2, pp. 349-356, Feb. 2011.

Shen C.C. et al, "The effect of third harmonic transmit phasing on contrast agent responses for CTR improvement," (in eng), Phys Med Biol, vol. 53, No. 21, pp. 6179-6194, Nov. 7, 2008.

Simpson, D.H. et al, "Pulse inversion Doppler: a new method for detecting nonlinear echoes from microbubble contrast agents," (in eng), IEEE Trans Ultrason Ferroelectr Freq Control, vol. 46, No. 2, pp. 372-382, 1999.

Simpson, D.H. et al, "Techniques for perfusion imaging with microbubble contrast agents," IEEE Transactions on Ultrasonics, Ferroelectrics, and Frequency Control, vol. 48, No. 6, pp. 1483-1494, 2001.

Sylvester J. J., Thoughts on inverse orthogonal matrices, simultaneous sign successions, and tessellated pavements in two or more colours, with applications to Newton's rule, ornamental tile-work, and the theory of numbers. Philosophical Magazine, 1867.

Tiran, E., et al. "Multiplane wave imaging increases signal-to-noise ratio in ultrafast ultrasound imaging." Physics in Medicine & Biology 60.21 (2015): 8549.

* cited by examiner

METHODS FOR ENCODED MULTI-PULSE CONTRAST ENHANCED ULTRASOUND IMAGING

CROSS-REFERENCE TO RELATED APPLICATIONS

This application represents the national stage entry of International Application No. PCT/US2018/043829, filed on Jul. 26, 2018, which claims the benefit of U.S. Provisional Patent Application Ser. No. 62/537,107, filed on Jul. 26, 2017, and entitled "METHODS FOR ENCODED MULTI-PULSE CONTRAST ENHANCED ULTRASOUND IMAGING," which is herein incorporated by reference in its entirety.

BACKGROUND

The development of contrast-enhanced ultrasound ("CEUS") imaging brings great potential for many clinical applications, such as myocardial perfusion imaging and abdominal lesion characterization. The contrast agents used in these imaging techniques are usually encapsulated microbubbles utilized to improve the contrast between blood and tissue. In general, these microbubbles can provide strong nonlinear echoes under low mechanical index ("MI"), whereas the tissue signals are largely linear at low MI.

To better detect the nonlinear microbubble echoes, several sequences are widely used to suppress linear tissue signals, which include pulse inversion ("PI"), amplitude modulation ("AM"), or pulse inversion amplitude modulation ("PIAM") sequences. These microbubble imaging techniques generally involve exciting the contrast agents with a single pulse in each of two different transmission events (i.e., pulse-echo events). The pulse emitted in the second transmission event is generated by modifying the pulse polarity in PI sequences, the pulse amplitude in AM sequences, or both in PIAM sequences relative to the pulse emitted in the first transmission event.

In the PI, AM, and PIAM sequences, the reflected echo RF signals from these two transmission events are combined to selectively cancel the linear response from tissue and to amplify the nonlinear response from the contrast agents. However, it is has been reported by several groups that the tissue also exhibits significant nonlinear responses that cannot be neglected, even under low MI. Therefore, there remains a need to suppress both linear and nonlinear tissue signals in microbubble contrast imaging.

SUMMARY OF THE DISCLOSURE

The present disclosure addresses the aforementioned drawbacks by providing methods for contrast-enhanced ultrasound imaging. The method includes transmitting a first set of ultrasound pulses in a first transmission event to a region-of-interest that contains a microbubble contrast agent in a subject using an ultrasound system. The first set of ultrasound pulses includes at least two ultrasound pulses each having an amplitude and a polarity encoded according to a first entry in an encoding matrix. First ultrasound data are received with the ultrasound system following the transmission of the first set of ultrasound pulses. A second set of ultrasound pulses is transmitted in a second transmission event to the region-of-interest in the subject using the ultrasound system. The second set of ultrasound pulses includes at least two ultrasound pulses each having an amplitude and a polarity encoded according to a second entry in the encoding matrix. Second ultrasound data are received with the ultrasound system following the transmission of the second set of ultrasound pulses. First decoded data are generated by decoding the first ultrasound data using an inverse of the encoding matrix, and second decoded data are generated by decoding the second ultrasound data using the inverse of the encoding matrix. Difference data are generated by computing a difference between the first decoded data and the second decoded data, and an image of the subject is produced from the difference data.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Described here are methods for contrast-enhanced ultrasound imaging that implement coded multi-pulses in each of two different transmission events. Data acquired in response to the two different transmission events are decoded and combined. In some embodiments, the coded multi-pulses include two or more consecutive Hadamard encoded ultrasound pulses. In other embodiments, multiplane wave pulses can be used. Such multiplane wave pulses can be coded using Hadamard encoding, as one example. In addition, the multiplane wave pulses can be further coded using amplitude modulation or pulse inversion amplitude modulation techniques.

Figure 1:
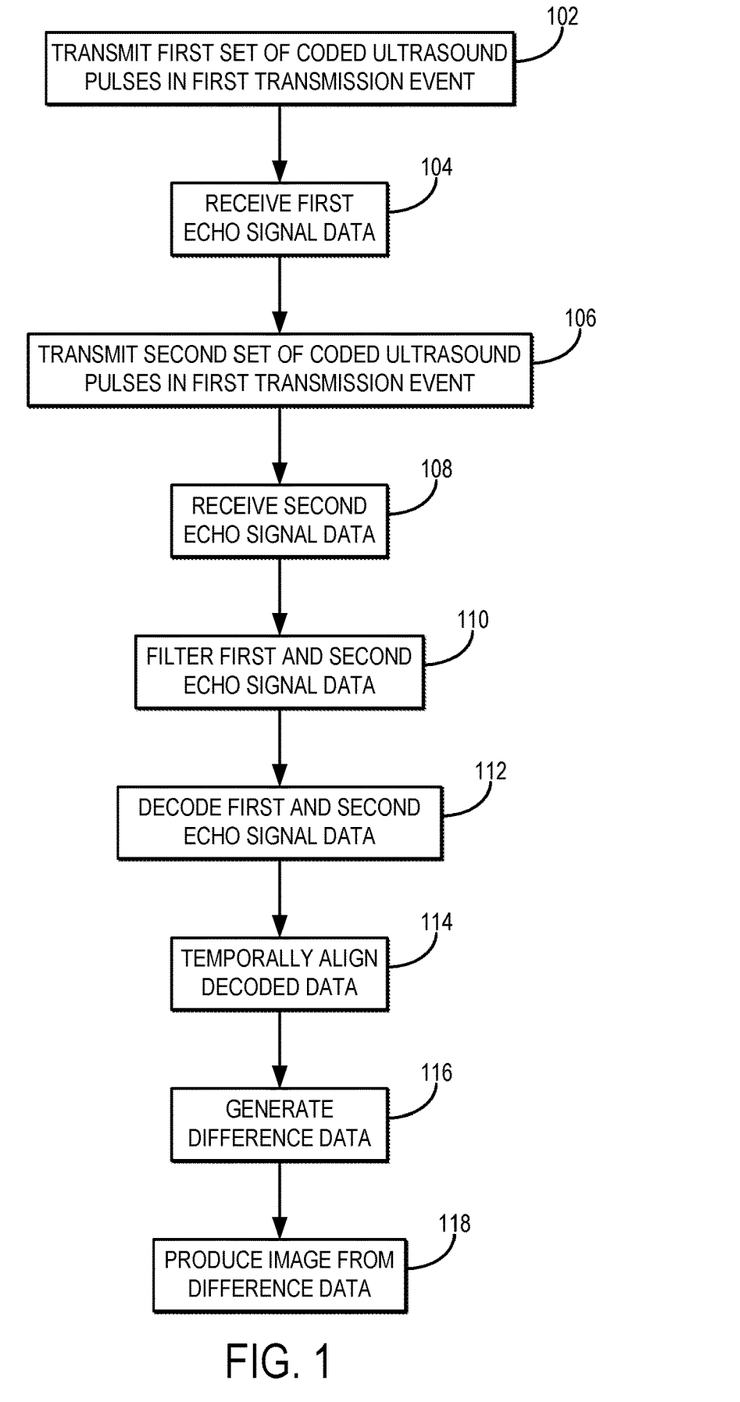
FIG. 1 is a flowchart setting forth the steps of an example method for contrast-enhanced ultrasound imaging using encoded multi-pulses in accordance with embodiments described in the present disclosure.

Referring now to FIG. 1, a flowchart is illustrated as setting forth the steps of an example method for contrast-enhanced ultrasound imaging using coded multi-pulses in consecutive transmission events. The method includes transmitting ultrasound pulses to a region-of-interest in a first transmission event, as indicated at step 102. In general, the ultrasound pulses are transmitted to a region-of-interest in which an ultrasound contrast agent is present. For example, a microbubble contrast agent can be administered to the subject being imaged such that the microbubble contrast agent is present in the region-of-interest when the ultrasound pulses are transmitted.

The ultrasound pulses are coded pulses. For instance, the ultrasound pulses can be coded according to a Hadamard encoding by adjusting the polarity of the ultrasound pulses based on coding factors in a Hadamard encoding matrix. As an example, the applied ultrasound pulses include two consecutive ultrasound pulses that are coded according to a second order Hadamard encoding matrix. In other embodiments, a coding matrix other than a Hadamard encoding matrix could be used, and a larger number of ultrasound pulses could be transmitted with the appropriate encoding (e.g., by using a higher order Hadamard or other coding matrix). In any event, the pulses that are transmitted in the first transmission event are coded according to a first entry in the encoding matrix. For instance, each row in the encoding matrix can correspond to a different transmission event, and each column in the encoding matrix can correspond to individual pulses. As such, the set of ultrasound pulses that are transmitted in the first transmission event are encoded according to a row in the encoding matrix, where each element in the row corresponds to a different encoding of a different pulse transmitted in the transmission event. A first set of echo signal data is then received in response to the ultrasound pulses transmitted to the region-of-interest in the first transmission event, as indicated at step 104.

In a second transmission event that follows the first transmission event, additional ultrasound pulses are transmitted to the region of interest, as indicated at step 106. As an example, the ultrasound pulses applied in the second transmission event also include two consecutive ultrasound pulses. In other embodiments, a coding matrix other than a Hadamard encoding matrix could be used, and a larger number of ultrasound pulses could be transmitted with the appropriate encoding (e.g., by using a higher order Hadamard or other coding matrix). In any event, the pulses that are transmitted in the second transmission event are coded according to a second entry in the encoding matrix. For instance, a different row of the encoding matrix can be used to encode the pulses transmitted in the second transmission event. A second set of echo signal data is received in response to the ultrasound pulses transmitted to the region-of-interest in the second transmission event, as indicated at step 108.

Compared to other microbubble imaging methods, the pulse length of the ultrasound pulses transmitted in steps 102 and 106 can be made longer by continuously transmitting multiple pulses in each transmission event, which can improve the nonlinear energy from microbubbles. In addition, using consecutive ultrasound pulses that are coded to have a fast change in polarity can excite strong nonlinear responses from the microbubbles. As one example, the combination of these factors can lead to an enhanced contrast-to-tissue ratio and signal-to-noise ratio compared to other contrast-enhanced ultrasound imaging methods.

In some embodiments, the ultrasound pulses that are transmitted in the first and second transmission event can implement coded multi-pulses, such as Hadamard encoded multi-pulses ("HEM"). The coded multi-pulses can be implemented in many different transmission modes, including standard plane wave compounding, focused beam, synthetic aperture imaging, and so on. In some other embodiments, the ultrasound pulses that are transmitted in the first and second transmission event can implement multiplane wave compounding, such as multiplane wave compounding using Hadamard encoded multi-pulses ("MW-HEM"). Examples of HEM and MW-HEM pulse sequences are described below in more detail.

The first and second sets of echo signal data can be filtered with a bandpass filter to eliminate certain frequency components, such as the second harmonic components from both the tissue and the contrast agents, as indicated at step 110. It is advantageous to use this bandpass filter because the use of a coded excitation tends to increase the tissue second harmonic response. Preferably, the bandpass filter is centered on the transmit center frequency (i.e., corresponding to a fundamental frequency). Because pulse inversion does not change the polarity of the second harmonic for Hadamard encoding, applying a bandpass filter to the echo signal data helps to reduce the tissue nonlinear responses.

The first and second sets of echo signal data are then decoded using the appropriate decoding matrix in order to generate first and second decoded signal data, as indicated at step 112. For instance, when the ultrasound pulses transmitted in the first and second transmission events are coded using a second order Hadamard encoding matrix, then Hadamard decoding is implemented to decode the echo signal data. The decoded RF signals can be viewed as data that would have been obtained from a pair of identical pulses emitted in two different transmission events with the same amplitude, pulse polarity, and steering angle.

The first and second decoded signal data are then temporally aligned, as indicated at step 114. As an example, the decoded signal data can be temporally aligned by applying a time shift corresponding to one pulse length.

Difference data are then generated by computing the difference between the first and second decoded signal data, after temporal alignment, as indicated at step 116. When multiplane wave compounding is implemented, a subtraction between each pulse pair corresponding to each steering angle is performed. The subtraction between the two decoded and realigned RF signals removes the tissue linear responses, whereas the nonlinear fundamental energy associated with the contrast agent is preserved.

Then one or more images are reconstructed, or otherwise produced, from the difference data, as indicated at step 118. As one example, coherent plane wave compounding can be implemented to form an image from the difference data.

Figure 2:
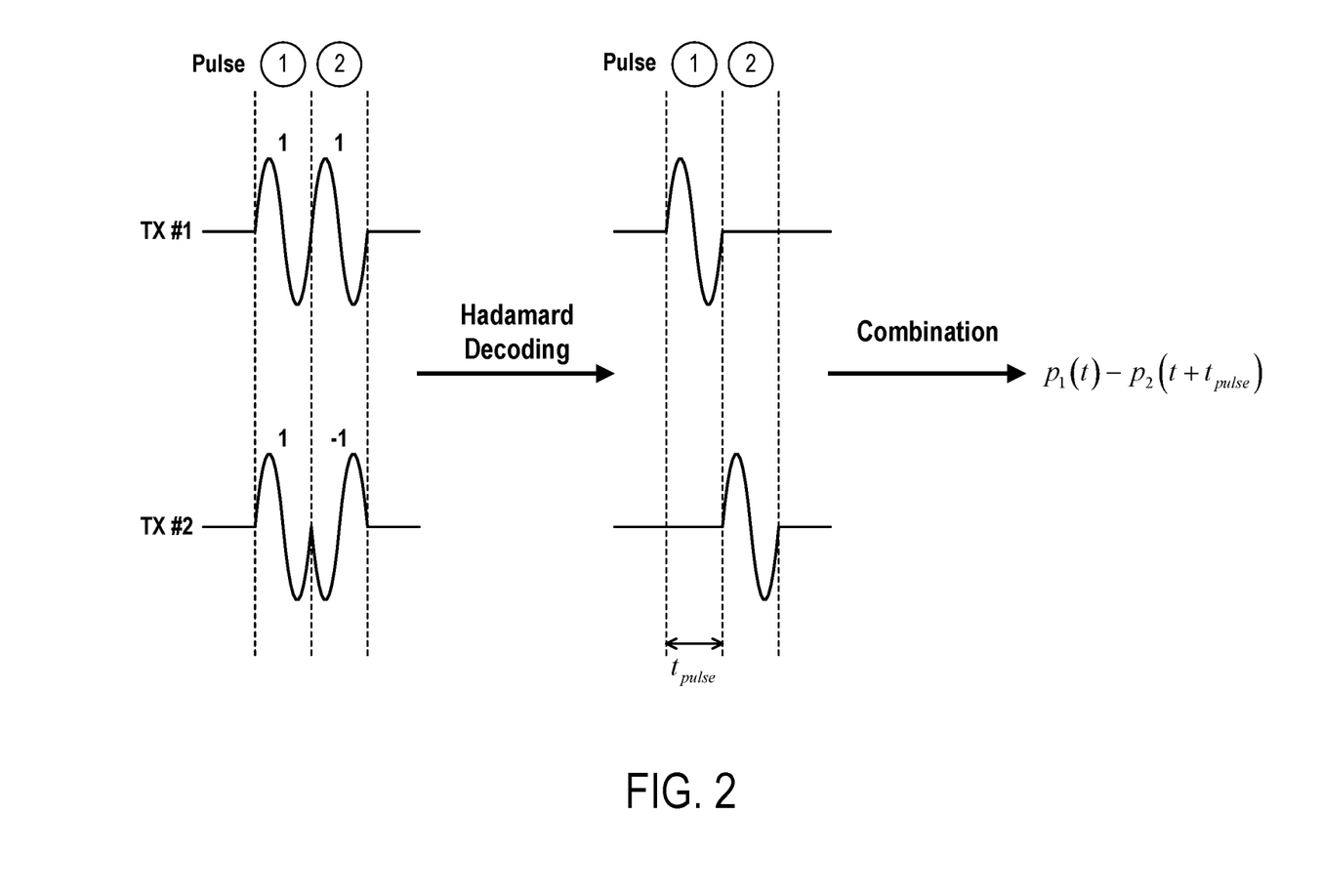
FIG. 2 illustrates an example of a Hadamard encoded multi-pulse transmission design. The sequence includes two transmission events (i.e., TX #1 and TX #2). Each transmission event contains two pulses (i.e., Pulse 1 and Pulse 2) emitted continuously. The sign of Pulse 2 in TX #2 is inverted following a second order Hadamard matrix. The received signals undergo standard Hadamard decoding. Then Pulse 1 and shifted Pulse 2 (by a pulse length axially, $t_{pulse}$) are subtracted to cancel the tissue responses.

Referring now to FIG. 2, an example of a Hadamard encoded multi-pulse ("HEM") pulse sequence design is shown. As described above, two or more ultrasound pulses are involved in the HEM sequence. In this example, two pulses (pulse 1 and pulse 2) are used. The ultrasound pulses are continuously emitted in both transmission events (TX #1 and TX #2). The extended pulse length resulting from the transmission of multiple pulses in each transmission event increases the transmitted energy. As a result, the reflected signal power from both contrast agents and tissue is increased. In this example, the two pulses are similar except that in the second transmission event (TX #2), the polarity of the second pulse is inverted following a second order Hadamard encoding. The fast sign change between the two pulses in the second transmission event excites strong nonlinear signals from microbubbles. This encoding process can be described as $$H_2 P = M;$$  (1)

or, as $$\begin{bmatrix} 1 & 1 \\ 1 & -1 \end{bmatrix} \begin{bmatrix} p_1 \\ p_2 \end{bmatrix} = \begin{bmatrix} m_1 \\ m_2 \end{bmatrix};$$  (2)

where $P=[p_1 \ p_2]^T$ is defined as the echo RF signals acquired with a single pulse emission (e.g., $p_1$ is the signal that would be acquired with transmitting the first pulse and without transmitting the second pulse) and M is the echo signal data received from the coded HEM emissions (e.g., $m_1$ is the combined signal received from the first and second pulses in the first transmission event, and $m_2$ is the combined signal received from the first and second pulses in the second transmission event).

As described above, a bandpass filter centered on the transmitted central frequency can be applied before Hadamard decoding. In one non-limiting example, this filtering is implemented to eliminate, or otherwise reduce, the second harmonic signals because these signals are not properly encoded and decoded by changing the pulse polarity of the fundamental signal. In many instances, the tissue harmonics (and primarily the second harmonic) can be relatively strong, even under low mechanical index. Therefore, the fundamental filter helps to further suppress the tissue signals. As described above, the filtered signal, M, undergoes Hadamard decoding, such as by multiplying M with the inverse of the Hadamard coding matrix, $H_2^{-1}$, to obtain P, $$P = H_2^{-1} M$$  (3).

After Hadamard decoding, P contains the signals as they would have been obtained by emitting the first and second ultrasound pulses individually in two separate transmission events. In this treatment, the two ultrasound pulses have the same amplitude and polarity except for a time delay, $t_{pulse}$, between them, as shown in FIG. 2. The linear response from tissue can be eliminated by selectively combining the signals $p_1$ and $p_2$. As described above, the signals $p_1$ and $p_2$ are first realigned in time. As one example, this temporal realignment can be accomplished by shifting the RF signal, $p_2$, axially along the fast time direction by a pulse length, $t_{pulse}$. The tissue linear response can then be cancelled by computing the difference between the signal from the first pulse and the temporally shifted signal from the second pulse, $$s = p_1(t) - p_2(t + t_{pulse})$$  (4).

In the example above, pulse 1 and pulse 2 are continuously emitted in both transmit events (i.e., TX #1 and TX #2). A small time gap, ε, can be inserted between pulse 1 and pulse 2. The tissue response is linear and should not change with choice of the time gap; therefore, the time gap can be selected to include strong microbubble nonlinear response in order to improve microbubble-to-tissue contrast. In general, the time gap, ε, should be sufficiently small such that microbubbles will not have completely returned to an equilibrium state following pulse 1 by the time that pulse 2 arrives. For example, the time gap can be 0.1 microseconds. If a time gap, ε, is used, then the time alignment step described above should be modified to also account for the small time gap. This small time gap can be implemented in any pulse sequence described in the present disclosure, but should not be confused with the time delay, Δt, described elsewhere in the present disclosure.

The example above uses a second order Hadamard encoding; however, as mentioned in the present disclosure, higher order encoding matrices can also be used. As one non-limiting example, a fourth order Hadamard encoding matrix can be used. In such an example, four transmission events would be implemented, each with four encoded pulses. After decoding and time alignment, four signals can be obtained. These signals can then be combined in various ways to cancel tissue linear response. For example, the difference between the data associated with any two pulses (e.g., pulse 1 and pulse 2, pulse 1 and pulse 3, pulse 2 and pulse 3) can be used. As another example, the difference between pulses can be accumulated, such as, $(p_1-p_2)+(p_3-p_4)$, $(p_1-p_3)+(p_2-p_4)$, or so on.

In another example, the time-aligned signals can be beamformed and converted through envelope detection to four different B-mode images, and the absolute difference between these B-mode images can be accumulated, such as, $|I_1-I_2|+|I_3-I_4|$, $|I_1-I_2|+|I_2-I_3|+|I_3-I_4|$, or so on. In yet another example, the square differences between these B-mode images can be accumulated, such as, $(I_1-I_2)^2+(I_3-I_4)^2$, $(I_1-I_2)^2+(I_2-I_3)^2+(I_3-I_4)^2$, or so on.

Figure 3:
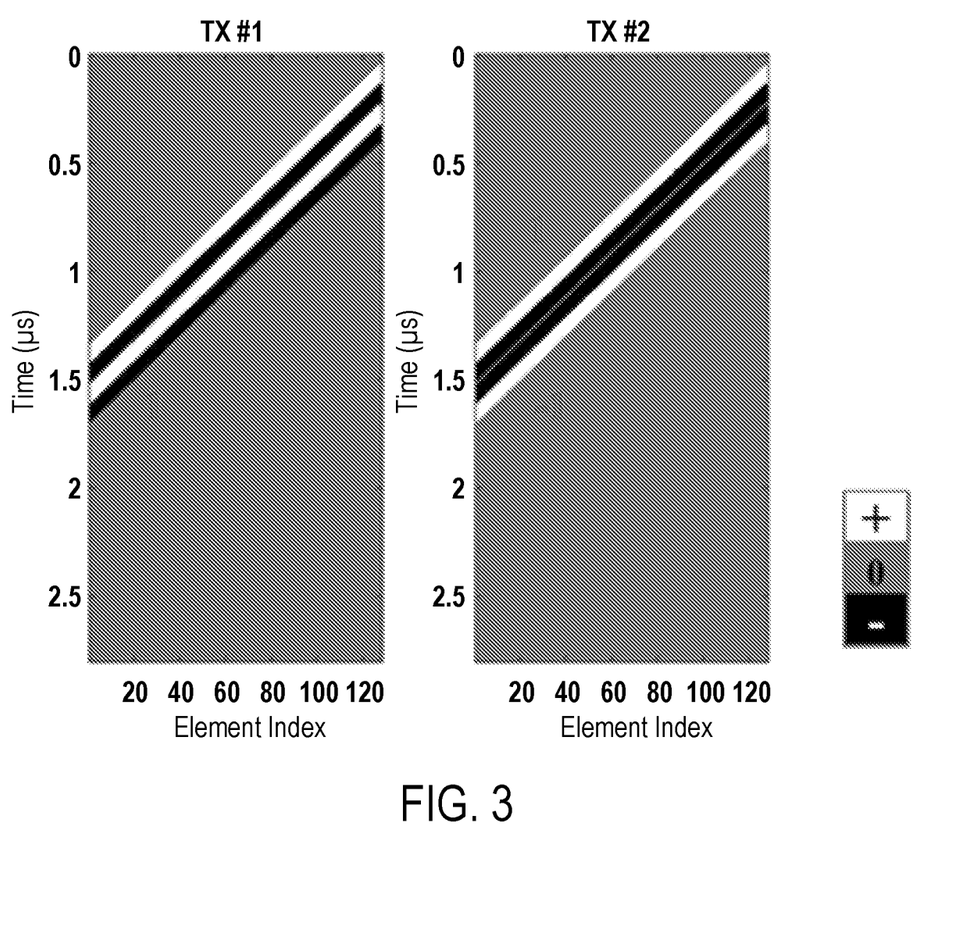
FIG. 3 illustrates a pair of transmission events of implementing an example HEM compounding sequence in contrast-enhanced ultrasound imaging a 3 degree steering angle using a tri-state pulser.

FIG. 3 shows an example of a pair of transmission events implementing an HEM imaging sequence in plane wave coherent compounding at a sample steering angle of three degrees. In FIG. 3, the [+, 0, −] in the legend represent the tristate pulses. The [1, −1] labeled below each wave stand for positive and negative (i.e., inverted) pulses, following Hadamard encoding. In each of the first and second transmission events, two pulses are emitted continuously at the same angle without a time gap between pulses. The polarities of the pulses follows the second order Hadamard matrix, similar to that in FIG. 2. Similarly, other transmission angles following the same excitation pattern can be obtained. Afterwards, the same decoding and recombination steps as described above can be applied to the received RF signals from all steering angles. The decoded and recombined signals corresponding to different steering angles can then be beamformed and summed coherently to perform compounding. Note that a "0" line of the tri-state pulser is inserted between the first and second pulse in transmission event #2 in order to separate these two pulses for better visualization. In real implementations, this "0" line can be discarded and thus a bi-state pulser with [+, −] can also be used.

Thus, one example implementation of the methods described in the present disclosure has been presented. In this example, the transmitted pulse length was doubled with a second order Hadamard coding matrix. This implementation led to higher transmitted energy and, thus, higher signal-to-noise ratio ("SNR"). Also, the fast sign change between Hadamard coded pulses in the second transmission event excited strong nonlinear responses from microbubbles to increase contrast between microbubbles and tissue. The methods described in the present disclosure thus provide and increased image SNR and contrast-to-tissue ratio ("CTR") relative to other commonly used microbubble imaging sequences such as PI, AM, and PIAM.

Compared to PI, the methods described in the present disclosure can image contrast agents mainly with the fundamental nonlinear components, such that frequency dependent attenuation is reduced, especially in deeper imaging regions. The spatial resolution in the methods described in the present disclosure may be reduced as compared to PI because of the lower imaging frequency band and longer pulse length. However, such resolution loss is balanced by the significantly improved image SNR and CTR. In addition, the methods described in the present disclosure may not require wide-bandwidth probes to provide good responses at both transmit and imaging frequency. Therefore, in some implementations the transmit and imaging frequencies can be selected to be at the center frequency of the probe to increase sensitivity.

Compared to AM and PIAM, the methods described in the present disclosure can achieve better SNR and CTR, as described above, especially in deeper imaging regions. The methods described in the present disclosure can provide lateral and axial resolutions comparable to those in AM and PIAM, which indicates that higher order Hadamard coding matrices could be implemented with the methods described in the present disclosure.

As described above, in some embodiments, multiplane wave imaging sequences can be adapted for use with the methods described in the present disclosure. Such applications are now described in more detail. As one example, the HEM sequence described above can be adapted to use multiplane wave pulses, yielding a multiplane wave HEM ("MW-HEM") sequence. As another example, amplitude modulation can be used in a coded multiplane wave sequence, yielding a multiplane wave amplitude modulation ("MW-AM") sequence. As still another example, pulse inversion amplitude modulation can be used in a coded multiplane wave sequence, yielding a multiplane wave pulse inversion amplitude modulation ("MW-PIAM") sequence.

In general, these multiplane wave sequences utilize a coding matrix with the following format, $$A = H_{2^k} \otimes B \qquad (5);$$

where A is the coding matrix, $H_{2^k}$ is a Hadamard coding matrix, and B is a set of base pulses. As an example, for MW-HEM, the base pulse can be a Hadamard encoded base pulse set, $B=H_2$; for MW-AM, the base pulse can be $B=[1, \frac{1}{2}]^T$; and for MW-PIAM, the base pulse can be $B=[1, -\frac{1}{2}]^T$.

These multiplane wave methods image microbubbles mainly with their reflected fundamental nonlinear energy, which can be extracted using a fundamental bandpass filter (i.e., a filter centered on the transmit center frequency). The received and filtered echo RF signals are decoded by multiplying themselves with the inverse of the corresponding coding matrices used in the different multiplane wave imaging cases. The decoded RF signals are equivalent to those as would have been obtained from a pair of identical pulses emitted in two different transmission events with the same amplitude, pulse polarity, and steering angle. Coherent plane wave compounding can then be applied to produce images from the difference data.

In the HEM multiplane wave imaging implementation described above, two coded pulses are emitted consecutively in each of two transmission events with the same steering angle. This HEM pulse sequence can be combined with multiplane wave transmissions for SNR gain. In the combination, the HEM pulse can be regarded as the base pulse and written in the pulse code format as, $$H_2 = \begin{bmatrix} 1 & 1 \\ 1 & -1 \end{bmatrix}. \qquad (6)$$

Each row of the pulse code corresponds to one transmission event whereas each column corresponds to the pulses emitted in different transmission events (i.e., each element in a column corresponds to one pulse). Then the HEM base pulse can be implemented in multiplane wave imaging through the Kronecker product as, $$A = H_{2^k} \otimes H_2 \qquad (7);$$

where k is the order of the Hadamard encoding matrix used in multiplane wave imaging, "$\otimes$" denotes the Kronecker product, and A is the encoding matrix for the MW-HEM sequence. Afterwards, this MW-HEM imaging process can be described as, $$AP = M \qquad (8);$$

where P is a column vector with elements of $p_{ij}$, which correspond to the echo RF signals acquired with the $i^{th}$ (i=1,2) pulse individually at the $j^{th}$ (j=j=1, . . . , J) steering angle. For example, $p_{j1}$ corresponds to the signal acquired with pulse 1 (without pulse 2) excitation under the first steering angle. In Eqn. (8), M is a column vector with elements of $m_l$, which correspond to the received echoes from the $l^{th}$ (l=1:L) MW-HEM transmission event. For example, $m_1$ corresponds to the received signals in the first transmission event of an MW-HEM sequence. In principle, the number of transmission events, L, can be selected as twice the number of steering angles, J.

Figure 4:
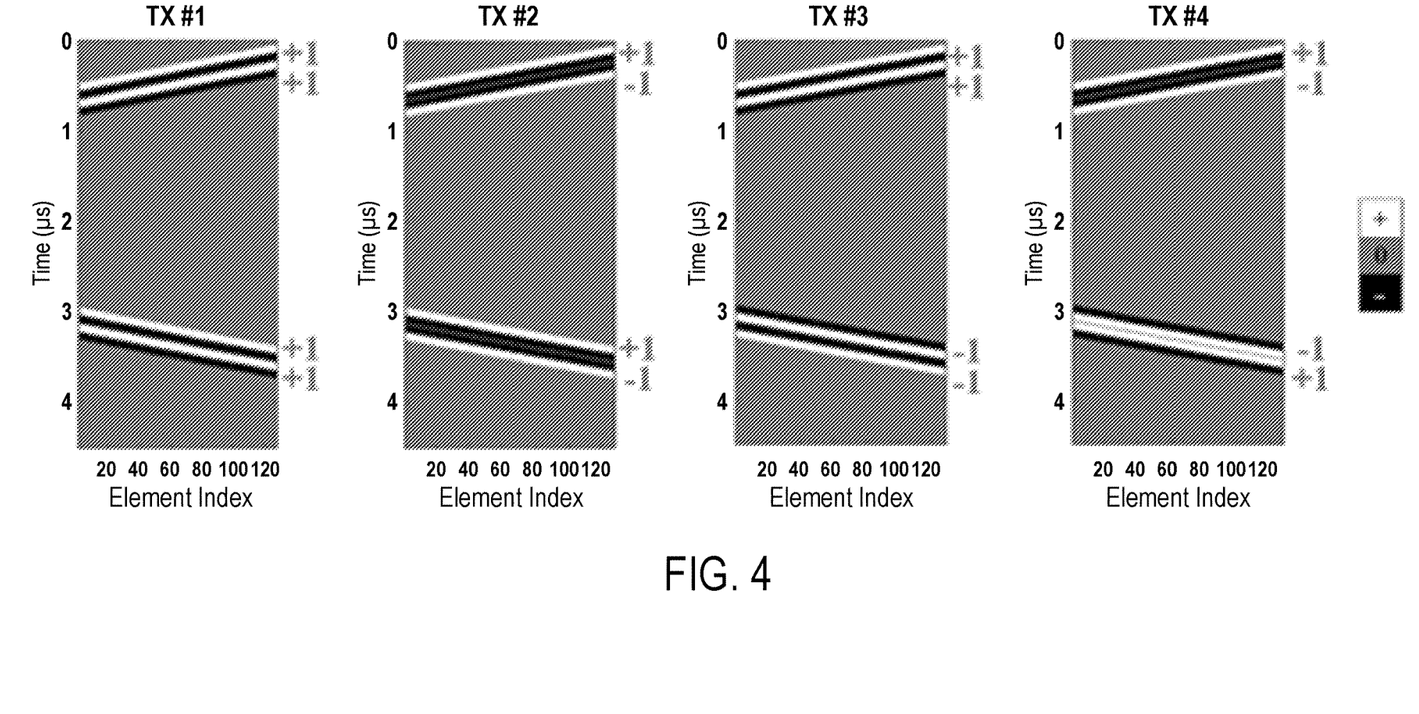
FIG. 4 illustrates a transmission pulse design for an example MW-HEM imaging sequence using a tri-state pulser. The sequence includes four transmission events (TX #1-TX #4), each of which contains two angled plane wave emissions as in MW imaging. Each angled emission contains two consecutive pulses as in the HEM sequence described in the present disclosure. A small interleaved time, Δt, is added between two angled plane wave emissions. No interleaved time is added between the two pulses for the same angle. Labelled beside each pulse is an indication of the polarities of emitted pulses for each angle in each transmission event.

FIG. 4 shows an example of an MW-HEM pulse sequence implementing second order Hadamard-encoded multiplane wave compounding. In this example, the encoding matrix is, $$A = H_2 \otimes H_2 = H_4 \quad (9).$$

With this encoding matrix, Eqn. (8) can be expanded as, $$\begin{bmatrix} 1 & 1 & 1 & 1 \\ 1 & -1 & 1 & -1 \\ 1 & 1 & -1 & -1 \\ 1 & -1 & -1 & 1 \end{bmatrix} \begin{bmatrix} p_{11} \\ p_{21} \\ p_{12} \\ p_{22} \end{bmatrix} = \begin{bmatrix} m_1 \\ m_2 \\ m_3 \\ m_4 \end{bmatrix}. \quad (10)$$

This example of an MW-HEM sequence contains four transmission events (i.e. TX #1-TX #4, L =4), each with two angled plane wave emissions (i.e., J=2). During each transmission event, between angled emissions, a short interleaved time Δt is added as in standard multiplane wave compounding. As one example, Δt can be selected as 1 μs. For proper decoding, the interleaved time, Δt, is preferably selected to be sufficiently long so as to allow microbubbles to return to a relative equilibrium following a previous pulse excitation. In addition, during each angled emission, two $H_2$-encoded pulses are excited consecutively with no interleaved time as in HEM imaging. The pulse polarities follow the assigned Hadamard factors based on Eqn. (9), which are labeled besides the emitted pulses in each transmission event in FIG. 4. Note that a "0" line of the tri-state pulser is inserted between the first and second pulse in transmission event #2 in order to separate these two pulses for better visualization. In real implementations, this "0" line can be discarded and thus a bi-state pulser with [+, −] can also be used.

Figure 5:
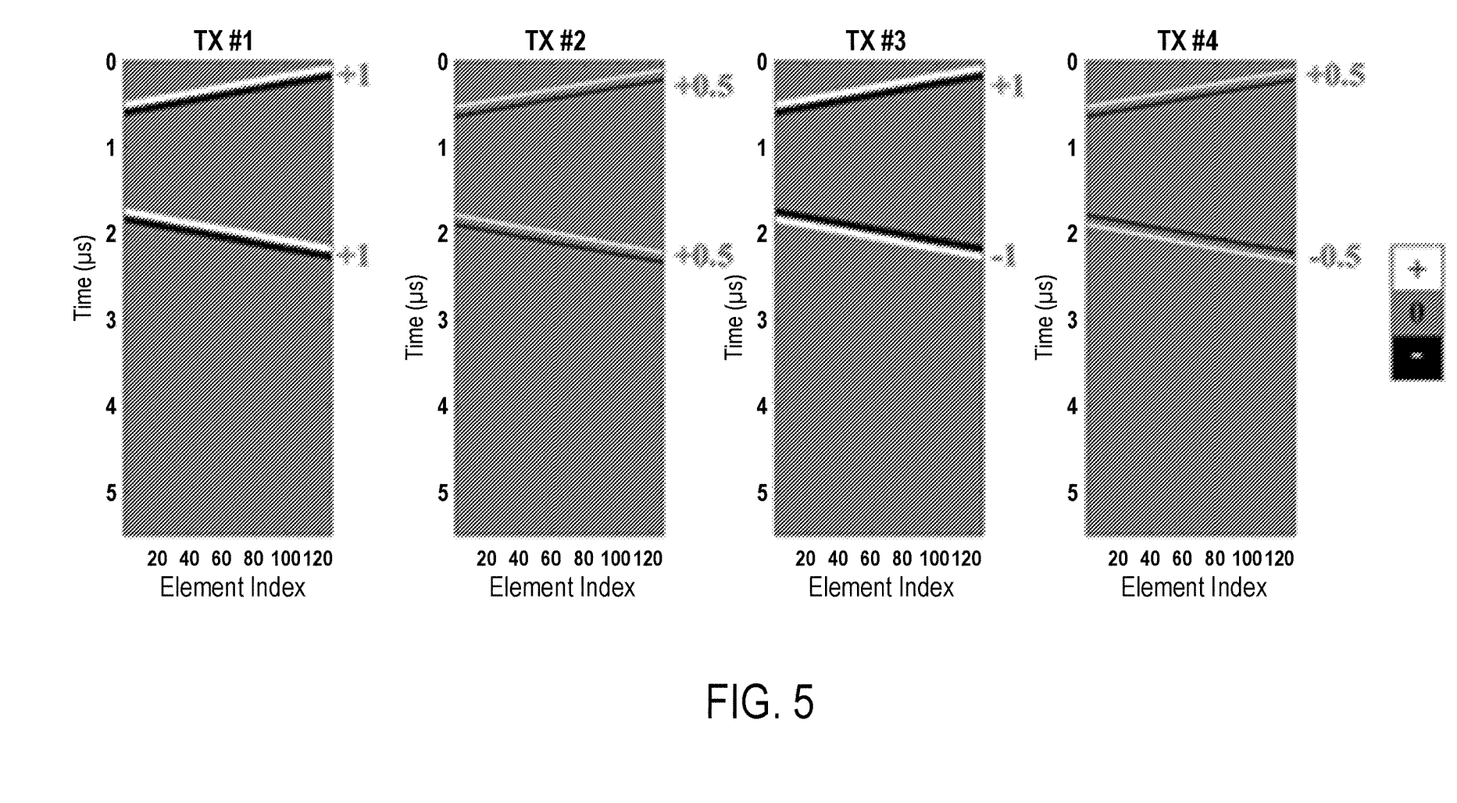
FIG. 5 illustrates a transmission pulse design for an example MW-AM imaging sequence using a tri-state pulser. The sequence includes four transmission events (TX #1-TX #4), each of which contains two angled plane wave emissions as in MW imaging. The amplitudes of the +1 and +½ pulses are reflected by the pulse duty cycles. A small interleaved time, Δt, is added between two angled plane wave emissions. Each angled emission only contains one pulse. The polarity and amplitude of a given pulse follows the coding matrix design as in Eqn. (11), which are labelled in red beside the pulses.
Figure 6A:
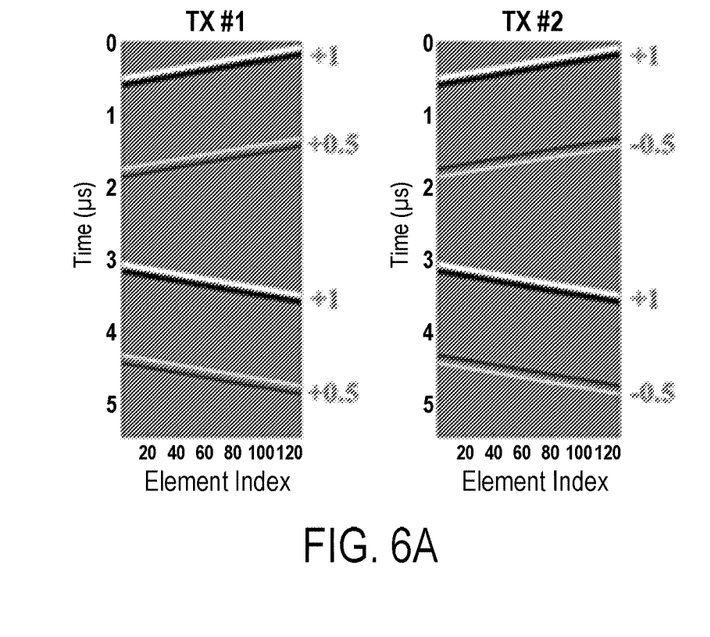
FIG. 6A illustrates a transmission pulse design for another example MW-AM imaging sequence using a tri-state pulser. Only the first transmission events (i.e., TX #1 and TX #2) are shown. Each transmission event contains four angled plane wave emissions, with the amplitude and polarity following the coding matrix as in Eqn. (12). The amplitudes of +1 and +½ pulses are reflected by the pulse duty cycles. A small interleaved time, Δt, is added between adjacent pulse emissions. Each angled emission contains a single pulse.
Figure 6B:
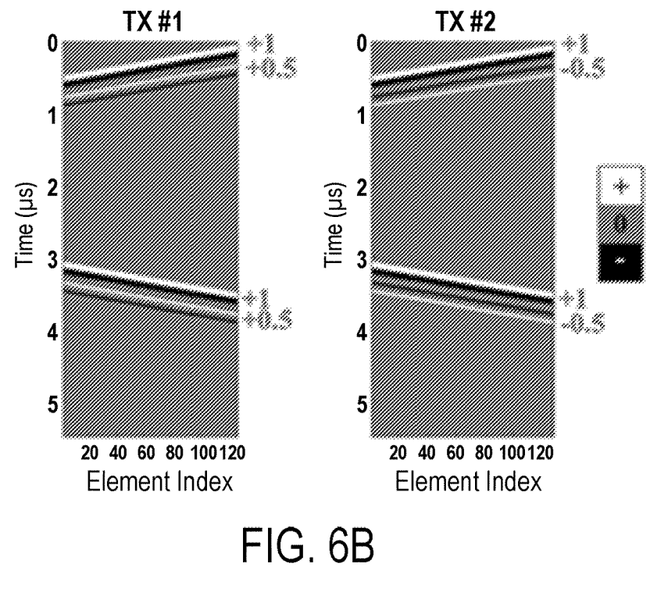
FIG. 6B illustrates a transmission pulse design for another example MW-AM imaging sequence using a tri-state pulser. Only the first transmission events (i.e., TX #1 and TX #2) are shown. Each transmission event contains four angled plane wave emissions, with the amplitude and polarity following the coding matrix as in Eqn. (12). The amplitudes of +1 and +½ pulses are reflected by the pulse duty cycles. The small interleaved time, Δt, between emissions with the same angle, but different pulses, is reduced to zero. Each angled emission contains two consecutive coded pulses.

In both the MW-AM and MW-PIAM sequences, the multiplane wave compounding can be adapted in different cases, which are summarized in Table 1 and described below in more detail.

TABLE 1

|  | Case 1 | Case 2 | Case 3 |
|---|---|---|---|
| Two base pulses encoding | Separately | Together | Together |
| Δt between different steering angles | Δt | Δt | Δt |
| Δt between same steering angles | N/A | Δt | 0 |
| Related FIGS. | FIG. 5 | FIG. 6A | FIG. 6B |

Similar to the MW-HEM sequence, the MW-AM and MW-PIAM sequences can use base pulses written in a pulse code format and combined with multiplane wave imaging via a Kronecker product. For example, in MW-AM, the following coding matrix can be used, $$A = H_{2^k} \otimes [1, 1/2]^T = \begin{bmatrix} 1 & 1/2 & 1 & 1/2 \\ 1 & 1/2 & -1 & -1/2 \end{bmatrix}^T. \quad (11)$$

As another example, pulse inversion amplitude modulation can be used in an $H_2$-encoded multiplane wave sequence, in which case the $[1, 1/2]^T$ base pulse in Eqn. (11) is replaced with the $[1, -1/2]^T$ base pulse.

Again, each row of the pulse code corresponds to one transmission event whereas each element in a given row corresponds to the one emitted pulse in a given transmission event. The coding matrix in Eqn. (11) is shown in the transpose format to match the emitted pulses vertically along the time direction in each transmission event, as in the pulse design example shown in FIG. 5. For such an MW-AM sequence, the two base pulses (i.e., +1 and +½ pulses) are emitted separately in different transmission events, as opposed to MW-HEM where the two coded pulses are emitted continuously in each angled emission during the same transmission event. Correspondingly, the number of columns of the MW-AM coding matrix is halved as compared to that in MW-HEM due to single base pulse excitation during each angled emission. Consequently, it is equivalent to the +1 and the +½ base pulses being encoded separately, each following the same $H_2$ To further increase the transmit energy, the two base pulses in MW-AM and MW-PIAM sequences can be encoded together in each of the transmission events, rather than separately as in FIG. 5.

For the MW-AM sequence described as case 2 in Table 1, the coding matrix can be constructed by first generating a fourth order Hadamard matrix, and then reducing the value of the even columns in this matrix to half as, $$A_{MW-AM} = \begin{bmatrix} 1 & 1 & 1 & 1 \\ 1 & -1 & 1 & -1 \\ 1 & 1 & -1 & -1 \\ 1 & -1 & -1 & 1 \end{bmatrix} \cdot \begin{bmatrix} 1 & 1 & 1 & 1 \\ 1/2 & 1/2 & 1/2 & 1/2 \\ 1 & 1 & 1 & 1 \\ 1/2 & 1/2 & 1/2 & 1/2 \end{bmatrix}^T \quad (12)$$

$$= \begin{bmatrix} 1 & 1 & 1 & 1 \\ 1/2 & -1/2 & 1/2 & -1/2 \\ 1 & 1 & -1 & -1 \\ 1/2 & -1/2 & -1/2 & 1/2 \end{bmatrix}^T;$$

where "⊗" denotes the element-wise product between matrices. For MW-PIAM, the coding matrix can be constructed as follows, $$A_{MW-PIAM} = \begin{bmatrix} 1 & 1 & 1 & 1 \\ 1 & -1 & 1 & -1 \\ 1 & 1 & -1 & -1 \\ 1 & -1 & -1 & 1 \end{bmatrix} \cdot \begin{bmatrix} 1 & 1 & 1 & 1 \\ -1/2 & -1/2 & -1/2 & -1/2 \\ 1 & 1 & 1 & 1 \\ -1/2 & -1/2 & -1/2 & -1/2 \end{bmatrix}^T \quad (13)$$

$$= \begin{bmatrix} 1 & 1 & 1 & 1 \\ -1/2 & 1/2 & -1/2 & 1/2 \\ 1 & 1 & -1 & -1 \\ -1/2 & 1/2 & 1/2 & -1/2 \end{bmatrix}^T.$$

FIG. 6A shows the first two transmission events based on this case 2 MW-AM design. The two base pulses are encoded together in all transmission events instead of separately in different transmission events, as in case 1. The amplitudes of +1 and +½ pulses are reflected by the pulse duty cycles in the figure. In some embodiments, a +½ pulse can be implemented by emitting ultrasound with only half of the transducer elements, such as with the odd numbered transducer elements. A short interleaved time, Δt, is added between each two adjacent pulse emissions.

FIG. 6B shows the MW-AM transmission pulse design example described as case 3 in Table 1. As inspired by MW-HEM, the interleaved time, Δt, between the same angled plane wave emissions can be reduced to zero as those in FIG. 4, aiming at higher microbubble nonlinear energy excitation with fast polarity and amplitude changes between coded pulses.

Note that for MW-AM in cases 2 and 3, the same coding matrix as shown in Eqn. (12) is followed; however, different transmission pulse designs are used, as shown in FIGS. 6A and 6B, respectively, based on the interleaved time between pulse emissions.

Similarly, Eqn. (13) shows the coding matrix design of PIAM implemented in the same MW compounding as in Eqn. (12). The comparison between Eqns. (12) and (13) illustrates that the MW-AM and MW-PIAM in cases 2 and 3 are equivalent. Only the order of transmission events varies. However, this principle does not apply for case 1. In the following description, the MW-AM sequences in the three different cases described above will be referred to as MW-AM1, MW-AM2, and MW-AM 3, respectively.

After MW-HEM, MW-AM, or MW-PIAM transmissions, a bandpass filter centered on the transmit center frequency is first applied to the received RF signals to eliminate second harmonic signals because they do not follow Hadamard encoding. Then, the filtered signals are decoded.

As one example, the decoding step can be accomplished by multiplying the echo RF signals received in coded MW excitations by the inverse of the coding matrix, $$P = A^{-1}M \qquad (14).$$

The decoded signals, P, $p_{1j}$ and $p_{2j}$, are similar to those obtained from exciting a pair of identical pulses (i.e., same polarity and amplitude) separately in two different transmission events at the same steering angle, j. The SNR, however, can be enhanced through the use of the MW encoding and decoding steps. After decoding, all pulse pairs are first re-aligned in time to compensate the interleaved time, Δt, introduced by the MW encoding and to compensate for the pulse length delay, $t_{pulse}$, as in MW-HEM or MW-AM3. This can be accomplished by shifting the decoded RF signals along fast time direction by the appropriate time determined by both Δt and $t_{pulse}$. Afterwards, the linear tissue signals can be suppressed through the subtraction between decoded and re-aligned pulse pairs as $p_{2j}-p_{1j}$. Note for MW-AM1 and MW-PIAM1, the +1 pulse and ±½ pulses can be decoded separately. In this example, an amplitude modulation of 0.5 was used; however, it will be appreciated that other amplitude modulated (e.g., 0.1, 0.25) can be used.

In addition, for AM or PIAM plane wave imaging, a checkerboard transmission pattern can be used. As an example, for AM a checkerboard transmission pattern may include three transmission events: firing all of the odd-numbered transducer elements, firing all of the even-numbered transducer elements, and firing the entire array. The summation of the returning echoes from the first two transmission events can be subtracted from the returning echoes from the third transmission event to cancel linear tissue signals. Checkerboard AM can improve linear signal cancellation and requires less hardware complexity. For checkerboard AM, the pulses in different single plane wave transmissions (i.e., odd, even, or full-element firing at different steering angles) can be divided into subgroups for MW encoding. For example, checkerboard AM with four compounding angles has 12 transmit pulses in total. These pulses can be divided into subgroups of 4 and 8, and then encoded by $H_4$ and $H_8$ matrices, respectively. Checkerboard AM can result in lower frame rate than AM with different pulse amplitudes.

Figure 7:
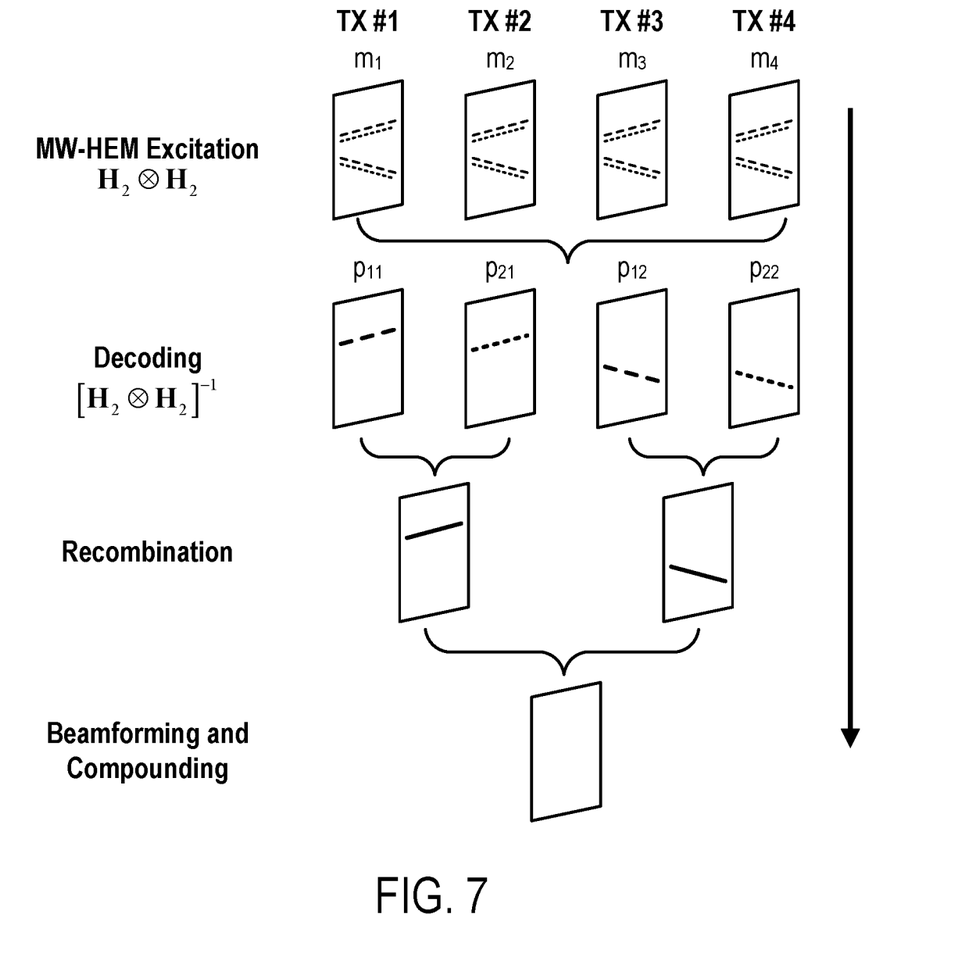
FIG. 7 illustrates an example MW-HEM transmission sequence and related processing pipeline. Hadamard encoded transmission events (e.g., HEM coded events) are excited sequentially in time. They contain the same plane wave emission angles, but different pulse polarities following the entries of Hadamard matrix. The received RF signals can be decoded into RF pairs. Each pair contains the emission angle excited with the same pulse. The subtraction between pulse pairs suppresses tissue linear responses. The decoded and recombined RF signals can be beamformed and compounded to produce a final image. The first row in this figure is a schematic representation of FIG. 4.

FIG. 7 shows a simplified schematic representation of the processes of MW-HEM sequence transmission, decoding, recombination, and compounding, respectively. The same four transmission events as shown in FIG. 4 are excited sequentially in time. The received RF signals, $m_i$, undergo the decoding process to recover the signals as would have been obtained with identical pulse pairs, $p_{1j}$ and $p_{2j}$ (shown with red and green lines in the second row, respectively), in standard plane wave imaging. The pulse pair recombination reduces tissue linear responses. Plane wave beamforming and compounding steps can then be applied to the re-aligned RF data from different angles to form the final compounded image.

Thus, different strategies for implementing contrast-enhanced ultrasound ("CEUS") pulse sequences in multiplane wave imaging, including MW-AM, MW-PIAM, and MW-HEM, have been described in the present disclosure. These MW-CEUS sequences mainly used the fundamental frequency band, which could be properly encoded and decoded by the Hadamard matrix. The microbubble signal contrast, SNR, and penetration depth were significantly improved after the combination. The methods described in the present disclosure can therefore extend the potential of CEUS imaging for different applications, such as imaging small vessels with weak flow or CEUS imaging with high frequencies when the frequency dependent attenuation dominates the microbubble detection efficiency.

Figure 8:
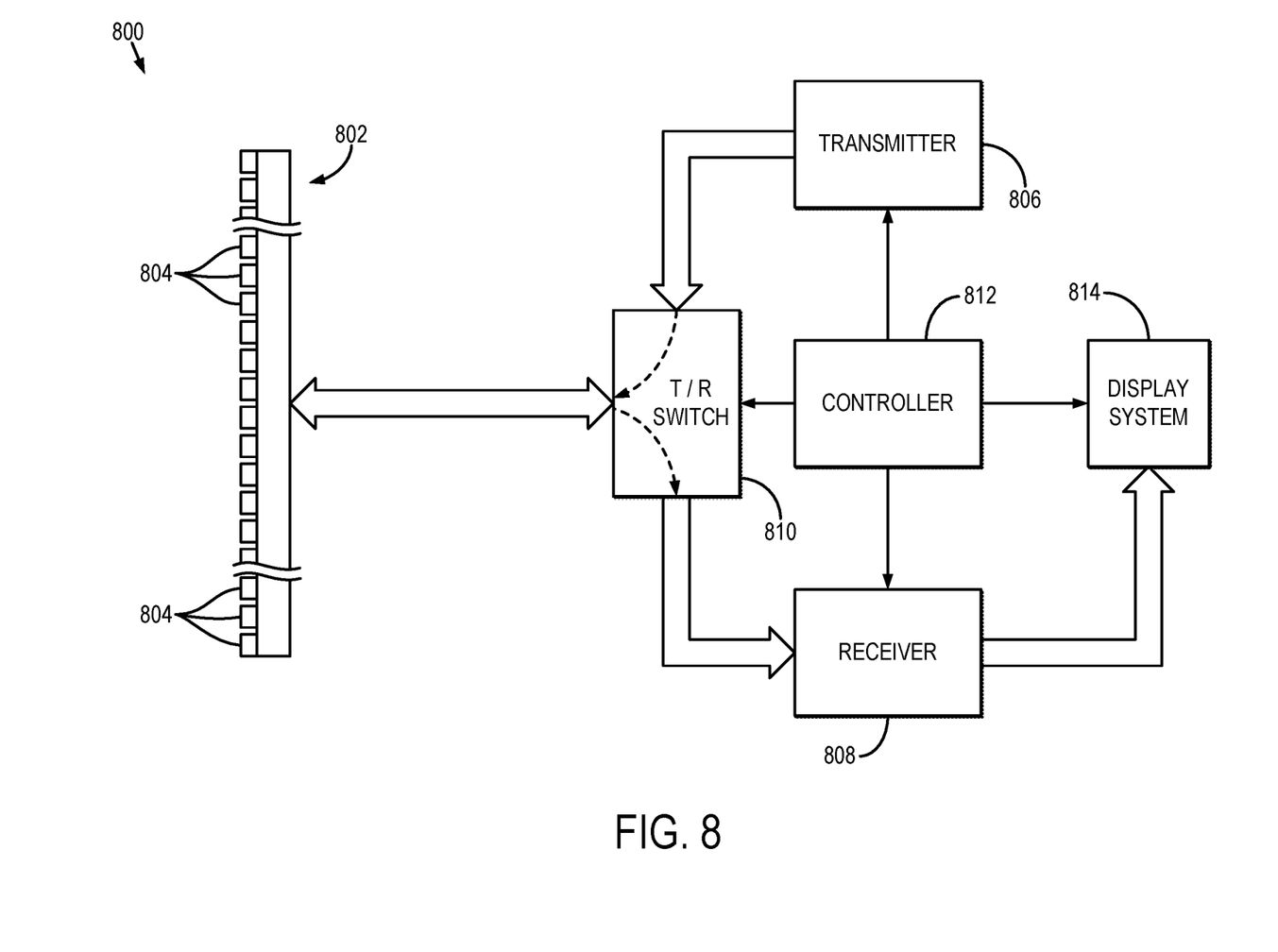
FIG. 8 is a block diagram of an example ultrasound system that can implement the methods described in the present disclosure.

FIG. 8 illustrates an example of an ultrasound system 800 that can implement the methods described in the present disclosure. The ultrasound system 800 includes a transducer array 802 that includes a plurality of separately driven transducer elements 804. The transducer array 802 can include any suitable ultrasound transducer array, including linear arrays, curved arrays, phased arrays, and so on. Similarly, the transducer array 802 can include a 1D transducer, a 1.5D transducer, a 1.75D transducer, a 2D transducer, a 3D transducer, and so on.

When energized by a transmitter 806, each transducer element 802 produces a burst of ultrasonic energy. The ultrasonic energy reflected back to the transducer array 802 from the object or subject under study (e.g., an echo) is converted to an electrical signal (e.g., an echo signal) by each transducer element 804 and can be applied separately to a receiver 808 through a set of switches 810. The transmitter 806, receiver 808, and switches 810 are operated under the control of a controller 812, which may include one or more processors. As one example, the controller 812 can include a computer system.

The transmitter 806 can transmit unfocused or focused ultrasound waves. In some configurations, the transmitter 806 can also be programmed to transmit diverged waves, spherical waves, cylindrical waves, plane waves, or combinations thereof. Furthermore, the transmitter 806 can be programmed to transmit spatially or temporally encoded pulses.

The receiver 808 can be programmed to implement a suitable detection sequence for the imaging task at hand. In some embodiments, the detection sequence can include one or more of line-by-line scanning, compounding plane wave imaging, synthetic aperture imaging, and compounding diverging beam imaging.

In some configurations, the transmitter 806 and the receiver 808 can be programmed to implement a high frame rate. For instance, a frame rate associated with an acquisition pulse repetition frequency ("PRF") of at least 100 Hz can be implemented. In some configurations, the ultrasound system 800 can sample and store at least one hundred ensembles of echo signals in the temporal direction.

The controller 812 can be programmed to design an imaging sequence using the techniques described in the present disclosure, or as otherwise known in the art. For example, the controller 812 can be programmed to design an imaging sequence based on an HEM sequence, and MW-HEM sequence, an MW-AM sequence, or an MW-PIAM sequence, as described above. In some embodiments, the controller 812 receives user inputs defining various factors used in the design of the imaging sequence.

A scan can be performed by setting the switches 810 to their transmit position, thereby directing the transmitter 806 to be turned on momentarily to energize each transducer element 804 during a single transmission event according to the designed imaging sequence. The switches 810 can then be set to their receive position and the subsequent echo signals produced by each transducer element 804 in response to one or more detected echoes are measured and applied to the receiver 808. The separate echo signals from each transducer element 804 can be combined in the receiver 808 to produce a single echo signal. Images produced from the echo signals can be displayed on a display system 814.

In some embodiments, the receiver 808 may include a processing unit, which may be implemented by a hardware processor and memory, to process echo signals or images generated from echo signals. As an example, such a processing unit can filter signal data, decode signal data, combine signal data, and produce images from signal data according to the methods described in the present disclosure.

The present disclosure has described one or more preferred embodiments, and it should be appreciated that many equivalents, alternatives, variations, and modifications, aside from those expressly stated, are possible and within the scope of the invention.

The invention claimed is:

1. A method for producing an image with an ultrasound system, the steps of the method comprising:
   (a) transmitting a first set of ultrasound pulses using the ultrasound system, wherein the first set of ultrasound pulses are transmitted in a first transmission event to a region-of-interest that contains a microbubble contrast agent in a subject, the first set of ultrasound pulses comprising at least two ultrasound pulses each having an amplitude and a polarity encoded according to a first entry in an encoding matrix;
   (b) receiving first ultrasound data with the ultrasound system following transmission of the first set of ultrasound pulses, wherein the first ultrasound signal data include first nonlinear signals from the microbubble content agent;
   (c) transmitting a second set of ultrasound pulses using the ultrasound system, wherein the second set of ultrasound pulses are transmitted in a second transmission event to the region-of-interest in the subject, the second set of ultrasound pulses comprising at least two ultrasound pulses each having an amplitude and a polarity encoded according to a second entry in the encoding matrix;
   (d) receiving second ultrasound data with the ultrasound system following transmission of the second set of ultrasound pulses, wherein the second ultrasound data included second nonlinear signals from the microbubble contract agent that are different from the first nonlinear signals;
   (e) generating first decoded data by decoding the first ultrasound data using an inverse of the encoding matrix, and generating second decoded data by decoding the second ultrasound data using the inverse of the encoding matrix;
   (f) generating difference data by computing a difference between the first decoded data and the second decoded data, wherein computing the difference between the first decoded date and the second decoded data results in removing a linear tissue response in the generated difference data; and
   (g) producing an image from the difference data.

2. The method as recited in claim 1, wherein the encoding matrix is a Hadamard encoding matrix.

3. The method as recited in claim 2, wherein the Hadamard encoding matrix is a second order Hadamard encoding matrix.

4. The method as recited in claim 1, wherein the encoding matrix comprises a Kronecker delta product between a base pulse set and a Hadamard encoding matrix.

5. The method as recited in claim 4, wherein the base pulse set comprises pulses encoded with a Hadamard encoding matrix.

6. The method as recited in claim 4, wherein the base pulse set comprises pulses modulated with an amplitude modulation.

7. The method as recited in claim 4, wherein the base pulse set comprises pulses modulated with a pulse inversion.

8. The method as recited in claim 4, wherein the base pulse set comprises pulses modulated with a pulse inversion amplitude modulation.

9. The method as recited in claim 1, wherein the first ultrasound data and the second ultrasound data are filtered with a bandpass filter at least one of before or after the first ultrasound data and the second ultrasound data are decoded.

10. The method as recited in claim 9, wherein the bandpass filter is centered on a transmit center frequency used when transmitting the first and second set of ultrasound pulses.

11. The method as recited in claim 1, wherein the first set of ultrasound pulses comprises a first set of multiplane wave ultrasound pulses and the second set of ultrasound pulses comprises a second set of multiplane wave ultrasound pulses.

12. The method as recited in claim 11, wherein the first set of multiplane wave ultrasound pulses includes multiplane wave pulses emitted at a first steering angle and a second steering angle, and the second set of multiplane wave ultrasound pulses also includes multiplane wave pulses emitted at the first steering angle and the second steering angle.

13. The method as recited in claim 1, wherein step (f) includes temporally aligning the first decoded data and the second decoded data before computing the difference between the first decoded data and the second decoded data.

14. The method as recited in claim 1, wherein at least one of the first set of ultrasound pulses or the second set of ultrasound pulses comprises a set of ultrasound pulses formed using at least one of plane wave compounding or synthetic aperture imaging.

15. The method as recited in claim 1, wherein at least one of the first set of ultrasound pulses or the second set of ultrasound pulses comprises focused ultrasound beams.

16. The method as recited in claim 1, wherein at least one of the first set of ultrasound pulses or the second set of ultrasound pulses comprises ultrasound pulses that are transmitted without a time gap between ultrasound pulses.

17. The method as recited in claim 1, wherein at least one of the first set of ultrasound pulses or the second set of ultrasound pulses comprises ultrasound pulses that are transmitted with a time gap inserted between ultrasound pulses.

18. A method for producing an image with an ultrasound system, the steps of the method comprising:
   (a) transmitting a first set of ultrasound pulses in a first transmission event to a region-of-interest that contains a microbubble contrast agent in a subject using an ultrasound system, the first set of ultrasound pulses comprising at least two ultrasound pulses each having an amplitude and a polarity encoded according to a first entry in an encoding matrix, wherein the first set of ultrasound pulses is transmitted in the first transmission event using a first subset of transducer elements of a transducer array of the ultrasound system;
(b) receiving first ultrasound data with the ultrasound system following transmission of the first set of ultrasound pulses;
(c) transmitting a second set of ultrasound pulses in a second transmission event to the region-of-interest in the subject using the ultrasound system, the second set of ultrasound pulses comprising at least two ultrasound pulses each having an amplitude and a polarity encoded according to a second entry in the encoding matrix, wherein the second set of ultrasound pulses is transmitted in the second transmission event using a second subset of transducer elements of the transducer array of the ultrasound system;
(d) receiving second ultrasound data with the ultrasound system following transmission of the second set of ultrasound pulses;
(e) transmitting a third set of ultrasound pulses in a third transmission event to the region-of-interest in the subject using the ultrasound system, wherein the third set of ultrasound pulses is transmitted using all of the transducer elements in the transducer array;
(f) receiving third ultrasound data with the ultrasound system following transmission of the third set of ultrasound pulses;
(g) generating first decoded data by decoding the first ultrasound data using an inverse of the encoding matrix, and generating second decoded data by decoding the second ultrasound data using the inverse of the encoding matrix;
(h) generating combined data by summing the first decoded data and the second decoded data;
(i) generating difference data by computing a difference between the combined data and the third ultrasound data; and
(j) producing an image from the difference data.

19. The method as recited in claim 18, wherein the first subset of transducer elements comprises odd-numbered transducer elements of the transducer array and the second subset of transducer elements comprises even-numbered transducer elements of the transducer array.

* * * * *